United States Patent [19]

Smith

[11] Patent Number: 5,766,194
[45] Date of Patent: Jun. 16, 1998

[54] SURGICAL APPARATUS FOR TISSUE REMOVAL

[75] Inventor: Sidney Paul Smith, Savannah, Ga.

[73] Assignee: Georgia Skin and Cancer Clinic, PC, Savannah, Ga.

[21] Appl. No.: 772,105

[22] Filed: Dec. 23, 1996

[51] Int. Cl.[6] .................................................. A61B 17/32
[52] U.S. Cl. .................................................. 606/167; 606/1
[58] Field of Search .............................. 601/46, 76, 154, 601/155, 163; 604/19, 22, 35; 606/1, 79, 110, 167, 169, 171, 159, 128

[56] References Cited

U.S. PATENT DOCUMENTS

| | | |
|---|---|---|
| 3,818,913 | 6/1974 | Wallach . |
| 3,930,505 | 1/1976 | Wallach . |
| 4,024,866 | 5/1977 | Wallach . |
| 4,898,574 | 2/1990 | Uchiyama et al. . |
| 4,913,698 | 4/1990 | Ito et al. . |
| 5,037,431 | 8/1991 | Summers et al. . |
| 5,320,599 | 6/1994 | Griep et al. ............ 606/159 |
| 5,322,504 | 6/1994 | Doherty et al. . |
| 5,338,292 | 8/1994 | Clement et al. . |
| 5,370,609 | 12/1994 | Drassler et al. . |
| 5,496,267 | 3/1996 | Drassler et al. ............ 604/22 |

FOREIGN PATENT DOCUMENTS

WO 90/05493  5/1990  WIPO .

*Primary Examiner*—Glenn K. Dawson
*Attorney, Agent, or Firm*—Veal & Associates

[57] ABSTRACT

A surgical instrument includes an elongated member connected to both a suction device for removing excised tissues and fluids and to a source of pressurized fluid. The member has an inner and outer wall with a hollow lumen extending the length of the member which connects a variably shaped ostium, extending through both walls of the member, to the suction means. The member also has peripheral channels extending the length of the member which connect the fluid source to the ostium through slits in the perimeter of the ostial wall. The slits collectively extend almost the full perimeter of the ostial wall. The slits are preferably designed so that as pressurized fluid is ejected from any point along a slit across the ostium, the fluid will come in contact with an opposing spray of fluid ejected from an opposing point in an opposing slit. The two sprays simultaneously applied across the ostium prevent the tissue from being pushed away by either spray, which in conjunction with a suction force, act to hold the tissue within the ostium as it is cut. Slit-type openings impart superior tissue cutting features compared to the nozzle-type openings of prior art devices because the cutting surface of the spray is elongated. The present invention can utilize a continuous stream from opposing slits, synchronized pulsations from opposing slits, alternating pulsations, or any combination thereof, and the frequency and intensity of the sprays can be varied to optimize tissue removal.

23 Claims, 4 Drawing Sheets

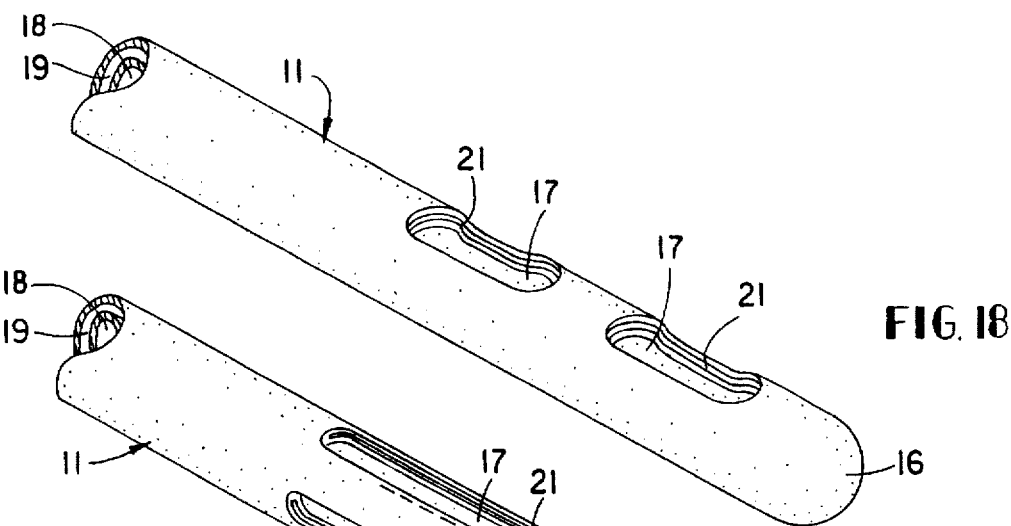
FIG. 18
FIG. 19
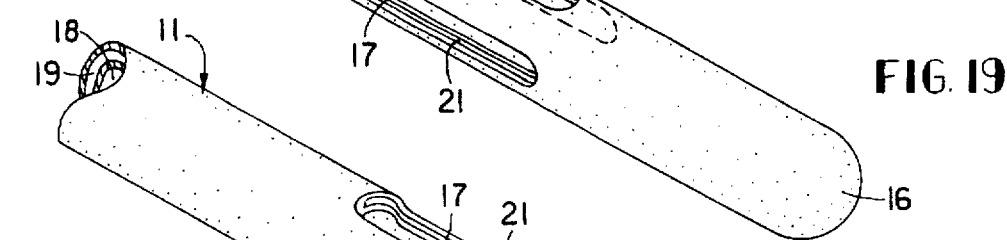
FIG. 20
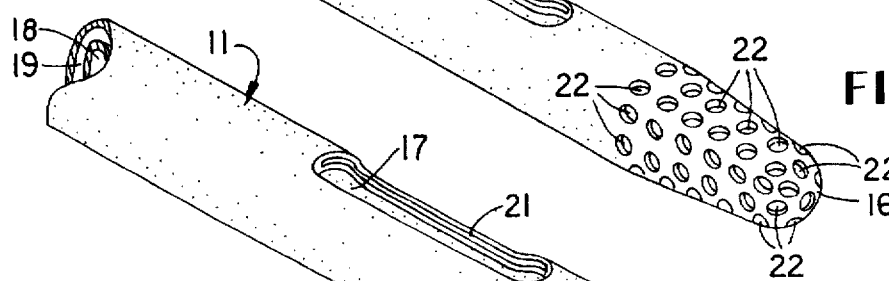
FIG. 21
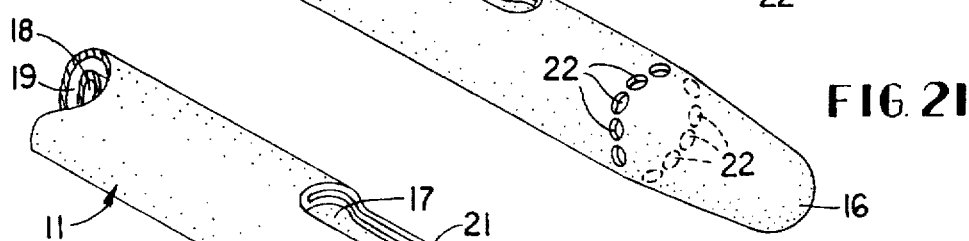
FIG. 22
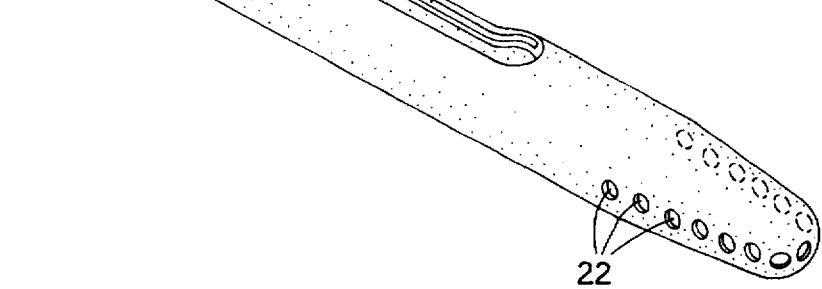

SURGICAL APPARATUS FOR TISSUE REMOVAL

FIELD OF THE INVENTION

The present invention relates to an apparatus for selectively removing bodily tissues. More particularly, the present invention relates to a surgical instrument which utilizes fluid forces to more effectively and safely remove tissues from the body.

BACKGROUND OF THE INVENTION

All structures have their own unique "natural" or "resonant" frequency which is the physical vibration point at which a structure will exhibit violent, even self-destructive vibrations. Those destructive vibrations occur as energy at a specific frequency is applied to an object. A common household example is the washing machine. When a washing machine enters its spin cycle, the wash load must be relatively evenly balanced about the drum. Otherwise, as the drum spins faster and faster, a strong vibrational force will be produced. As this vibration nears the unique natural frequency of the washing machine, the machine will shake violently. If the vibration remains at this frequency, the machine will likely shake itself apart.

Another historical example of destructive resonant vibration on a larger scale is the Tacoma Narrows Bridge disaster in Tacoma, Wash. The bridge was designed as a suspended plate girder bridge and as a result caught wind passing through the span. As the wind intensity increased on Nov. 7, 1940, to 42 m.p.h., a continuous oscillation or rocking motion was created throughout the span of the bridge that grew in intensity until the bridge finally tore apart. Like a washer and the Tacoma Bridge, organs and tissues in the human body have natural resonant frequencies at which they will resonate, resulting in tissue specific destruction.

Various medical devices have been created for removing body tissues and in particular, fat. The differences between these devices essentially depends upon the physical properties of the instrument and the particular tissue to be removed. For example, an ultrasonic device (using high frequency sound waves) can be used to break apart a kidney stone but would have little to no effect on less dense objects such as fat or muscle. A kidney stone is compact and a high frequency ultrasound device can break the stone into smaller pieces for removal. Body fat, on the other hand, is more like a firm gelatin and would simply wiggle if a sound wave was applied.

Some researchers have developed an ultrasonic cannula that vibrates rapidly, destroying neighboring tissue by "melting" the tissues. Unfortunately, nerve, artery and tissue burns result at the ultrasonic frequencies required to break apart fat cells because these frequencies are not specific for fat. This results in scars and other unwanted side effects. Another example of a device used for removing tissue is a laser, which can be used, for example, in cutting atherosclerotic plaques from arteries. This device uses a light wave to incinerate an object, but again, because many tissues absorb laser energy, neighboring nerves and blood vessels are injured concomitantly with fat removal. These medical devices are not useful for removing fat because they employ ultrasonic and laser frequencies not specifically absorbed by fat.

Only when a device employs frequencies of energy at or near the natural frequency of a tissue can complete and safe removal be achieved. Fat, or adipose tissue, is unique in its physical characteristics, requiring a special technique for removal. Being a very distensible tissue, fat easily moves away from any applied force. Presently, the common technique for removing fat and other soft tissues from the body is suctioning tissues into a cannula and subsequent removal with a shearing force. This unfortunately results in excessive damage to lymphatics, nerves and blood vessels, as well as leading to scar formation. Currently, all cannulas used to remove soft tissues such as fat rely on such shearing forces.

As seen in the foregoing discussion, it is preferable for any medical device employed in tissue removal to address the unique "resonant" features of the tissue. As a result, there is a need for a new surgical instrument, designed to remove a variety of tissues, which has the versatility to address the unique resonant properties of the particular tissue, fat in particular, to optimize the removal while decreasing damage to neighboring tissues.

SUMMARY OF THE PRESENT INVENTION

It is the object of the present invention to provide an apparatus which is designed to remove various types of tissue from the body.

It is another object of the present invention to provide an apparatus which can utilize either opposing or non-opposing fluid forces across an ostium to more effectively remove tissues.

It is another object of the present invention to apply alternating fluid pulsations at or near the natural frequency of the tissue to be removed to allow specific tissue removal without damaging surrounding tissues having different natural frequencies.

It is another object of the present invention to use fluid forces which can be varied in intensity to optimize tissue removal depending on the unique physical properties of the tissue to be removed.

It is another object of the present invention to use fluid forces which can be varied in frequency of pulsations to optimize tissue removal depending on the unique physical properties of the tissue to be removed.

It is another object of the present invention to use fluid forces which can be alternated to set up a vibrational force or a simultaneously compressing force fluid wave which can be selected for the unique physical properties of the tissue to be removed.

It is another object of the invention to use forces which can vary in intensity, frequency and pattern of flow in a programmed pattern, such as a sine wave, with all variables fluctuating independently to meet all the natural frequencies of a given tissue to optimize tissue removal.

It is another object of the invention to use selective resonant frequencies of the tissue to be removed.

It is another object of the invention to use a washing mechanism to "clean" suctioned tissues and limit residual free fats to reduce scarring.

It is another object of the invention to use opposing fluid forces to insure complete removal of selective tissues.

It is another object of the invention to use fluid forces specifically directed to prevent tissue from escaping back into the body of the patient.

It is another object of the invention to use a unique water cutting surface to optimize tissue removal.

It is another object of the invention to enhance the efficiency of tissue removal to accelerate the procedure.

It is another object of the invention to use a less traumatic and scarring technique by applying resonant frequencies specific to the unique physical properties of the tissue to be removed.

It is another object of the invention to anesthetize the tissues to be removed concomitantly with liposuction.

It is another object of the invention to vary the angle and width of the fluid forces to optimize tissue removal.

These and other objects of the present invention are accomplished through the use of an improved surgical instrument comprising an elongated member, such as a cannula, connected at one end to both a suction means for removing excised tissues and fluids and to at least one source of pressurized fluid. An opposite end of the member has at least one variably shaped but preferably elliptically shaped ostium through its wall. The elongated member has an inner and an outer wall with a hollow lumen extending the length of the member and connecting the ostium to the suction means. The elongated member also has peripheral channels extending the length of the member which connect the pressurized fluid source to the ostium through slits around the perimeter of the ostial wall. The slits collectively extend from partially to substantially the full perimeter of the ostial wall. The slits can be situated so that as pressurized fluid is ejected from any point along a slit across the plane of the ostium, a spray of fluid will come in contact with an opposing spray of fluid ejected from an opposing point in an opposing slit. Alternatively, the slits can be situated to eject sprays of fluid into the lumen of the member at an angle between 0 and 90 degrees from the plane of the ostium. The elongated member can also have apertures which open through the outer wall of the member to allow pressurized fluid to pass directly into the tissues to assist in breaking up the tissues for removal.

In operation, pressurized fluid is forced through the channels and into the ostium from the opposing or non-opposing slits. Opposing sprays simultaneously or in an alternating frequency applied across the ostium, in conjunction with a suction force, act to prevent the tissue from being pushed away by either spray and cut the tissue. The slit-type openings of the present invention have superior tissue cutting qualities compared to the nozzle-type openings of prior art devices because the cutting surface of the spray is elongated, which may be analogized to a knife blade cutting surface compared to a needle point cutting surface. The excised tissue is then sucked down the lumen for removal. The present invention can utilize a continuous stream from opposing slits, synchronized pulsations from opposing slits, alternating pulsations, or any combination thereof including on/off periods. Additionally continuously variable dynamics of the force can be applied in sine wave patterns to encompass unique tissues which may be present in a given area. Various combinations of slits with varying angles of spray can be used. The frequency and intensity of the sprays can be varied, and can be greater from one slit than from the opposing slit. Additionally, the present invention can utilize alternating pulses to set up a vibrational force, or wave, directed to the unique vibrational characteristics of the particular tissue to be removed in order to selectively break down the tissue while minimizing damage to surrounding tissues.

These and other objects and advantages of the invention will become apparent from the following detailed description of the preferred embodiment.

BRIEF DESCRIPTION OF THE DRAWINGS

An apparatus embodying features of the invention is described in the accompanying drawings which form a portion of this disclosure and wherein:

FIG. 18 is a perspective view of another alternate embodiment of the apparatus.

FIG. 19 is a perspective view of another alternate embodiment of the apparatus.

FIG. 20 is a perspective view of another alternate embodiment of the apparatus.

FIG. 21 is a perspective view of another alternate embodiment of the apparatus.

FIG. 22 is a perspective view of another alternate embodiment of the apparatus.

DETAILED DESCRIPTION OF THE PREFERRED EMBODIMENT

Surgical instruments similar to the present invention are well known in the art. They are elongated thin members designed to reduce scarring by minimizing the length of the incision needed to perform the surgery. The present invention is an improvement over the prior art devices in that it can be used with different types of tissues, has superior tissue cutting features, causes less damage to neighboring tissue and is versatile to address the unique physical properties of the particular tissue which is to be excised. A more complete understanding of the invention may be obtained by reference to the accompanying drawings wherein the invention, according to the preferred embodiment, comprises an elongated tubular member 11. Member 11 can either be rigid, being comprised of aluminum, steel, titanium, etc., or it can be flexible, being comprised of a flexible polymer or the like.

Figure 17:
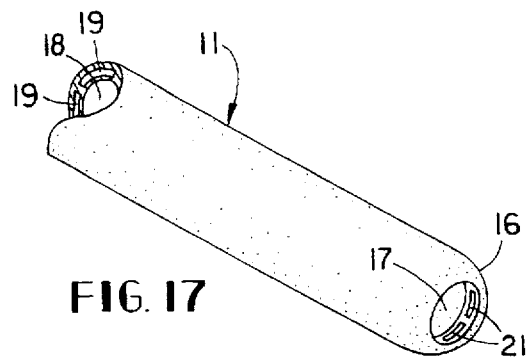
FIG. 17 is a perspective view of another alternate embodiment of the apparatus.

Member 11 has one end 12 connected to both a suction pump 13 for removing tissues and fluids and to at least one source of pressurized fluid 14 for providing fluids for tissue removal. Suction devices and pressurizing devices are well known in the medical arts and, therefore, will not be expounded herein. The fluids are preferably comprised of an isotonic solution possibly including antibiotics, epinephrine, bicarbonate, or lidocaine or other anesthetics to anesthetize the tissues concomitantly with liposuction, although various other non-toxic fluids or additives can also be used. Additionally, the fluids can include abrasive materials to assist in removing denser tissues. An opposite end 16 of member 11 preferably has a rounded tip, although it can be spoon-shaped, triangular, etc., and includes at least one ostium 17, preferably circular or elliptically shaped, through its wall. Ostium 17 can vary in shape, size and location depending on the size and type of tissue to be removed and its location within the patient's body. Ostium 17 is preferably along one side of member 11, but could also be located on the distal tip of end 16, shown in FIG. 17. Additionally, multiple ostia 17 can be aligned along elongated member 11, some examples of which are shown in FIGS. 18 and 19.

Figure 7:
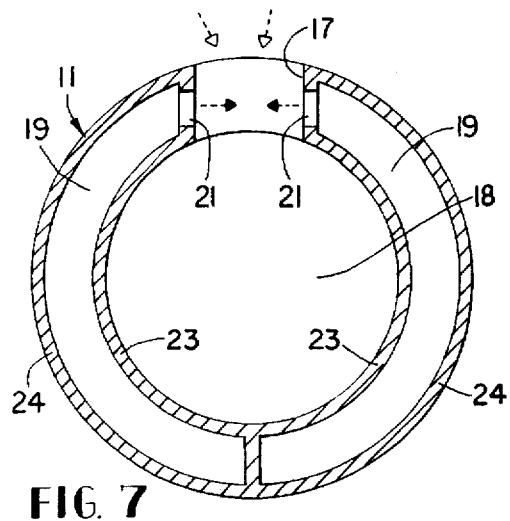
FIG. 7 is a sectional view taken along line 7—7 of FIG. 2.
Figure 14:
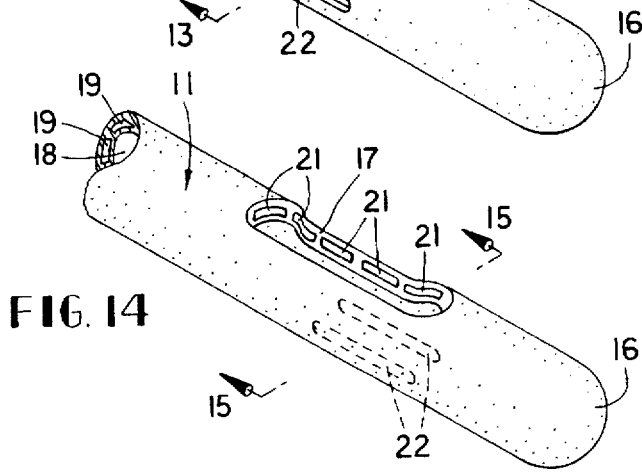
FIG. 14 is a perspective view of another alternate embodiment of the apparatus.
Figure 13:
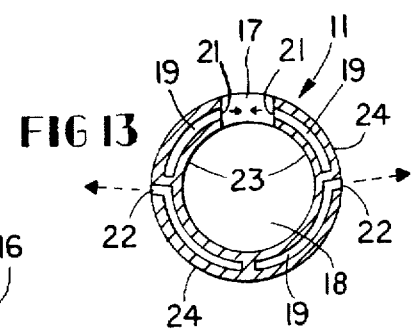
FIG. 13 is a sectional view taken along line 13—13 of FIG. 12.
Figure 15:
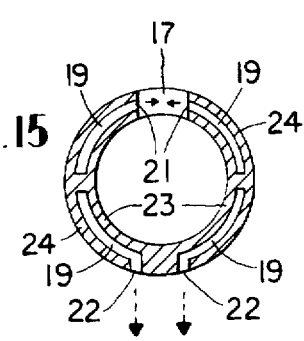
FIG. 15 is a sectional view taken along line 15—15 of FIG. 14.
Figure 16:
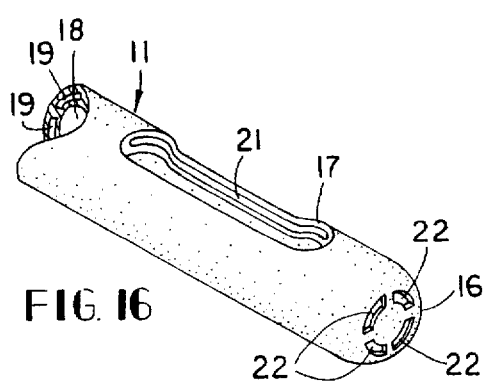
FIG. 16 is a perspective view of another alternate embodiment of the apparatus.

Member 11 has an inner wall 23 and an outer wall 24 with a hollow lumen 18 extending the length of the member and connecting ostium 17 to suction pump 13. Member 11 also has peripheral channels 19, best illustrated in FIGS. 5–10, extending the length of the member which connect pressurized fluid source 14 to ostium 17 through slits 21. The invention has at least one channel 19 terminating in at least one slit 21, which would preferably extend substantially around the entire circumference of the ostium; however, it is preferable to have at least two channels 19 terminating in at least two slits 21. Alternatively, channels 19 can terminate in a plurality of slits 21, as illustrated in FIG. 14. In any case, slits 21 collectively extend along almost the full perimeter of ostium 17 such that as pressurized fluid is ejected from any point along a slit and into the plane of the ostium, the fluid may come in contact with an opposing spray of fluid ejected from an opposing point in an opposing slit, best illustrated in FIG. 7.

Figure 1:
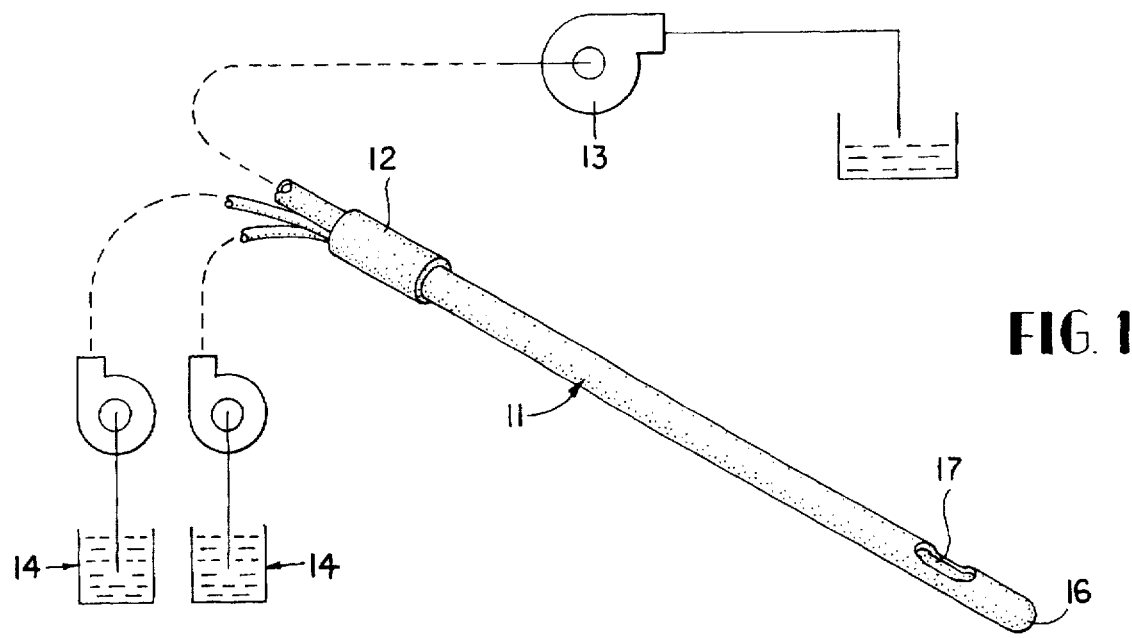
FIG. 1 is a perspective view of the apparatus.
Figure 2:
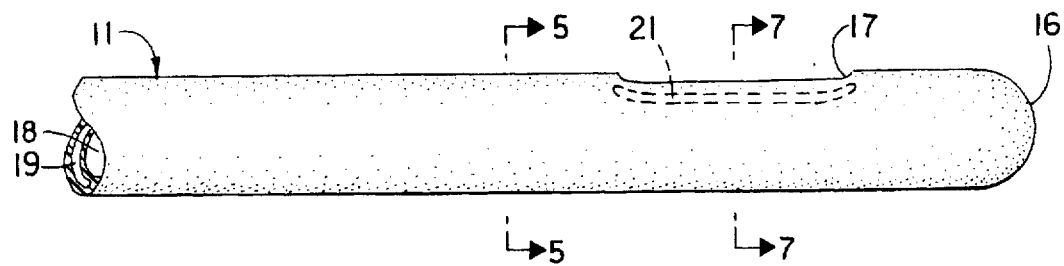
FIG. 2 is a side view of the apparatus.
Figure 3:
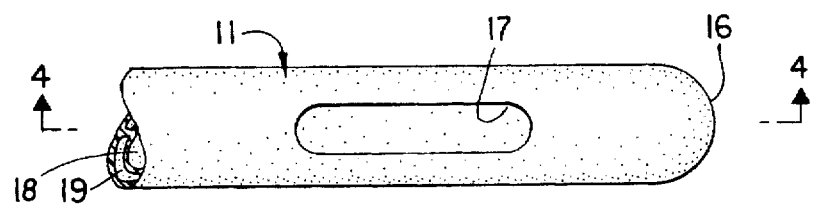
FIG. 3 is a top plan view of the apparatus.
Figure 4:
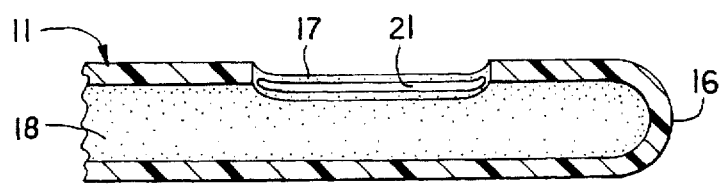
FIG. 4 is a sectional view taken along line 4—4 of FIG. 3.
Figure 5:
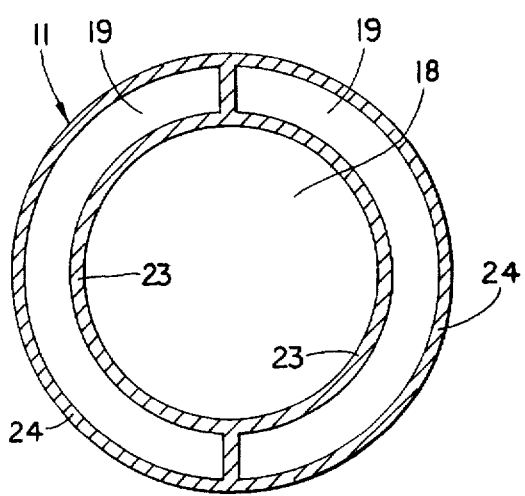
FIG. 5 is a sectional view taken along line 5—5 of FIG. 2.
Figure 8:
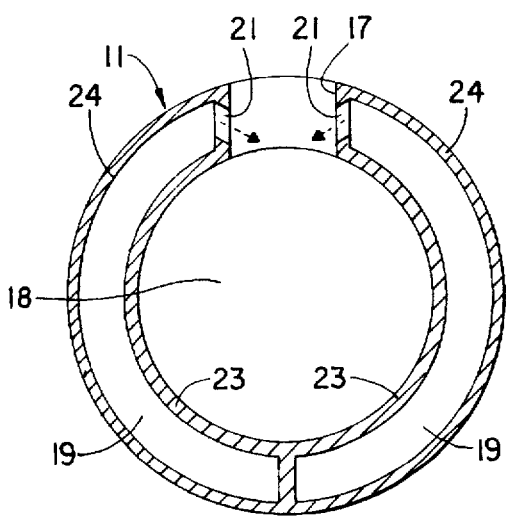
FIG. 8 is a cross-sectional view of an alternate embodiment of the apparatus showing a slit angle of approximately 45 degrees.
Figure 6:
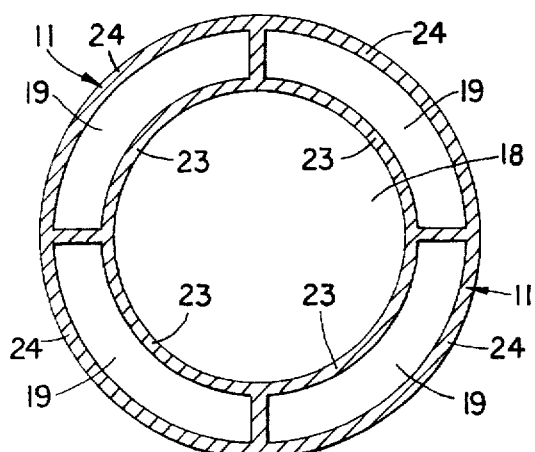
FIG. 6 is a cross-sectional view of an alternate embodiment of the apparatus.
Figure 9:
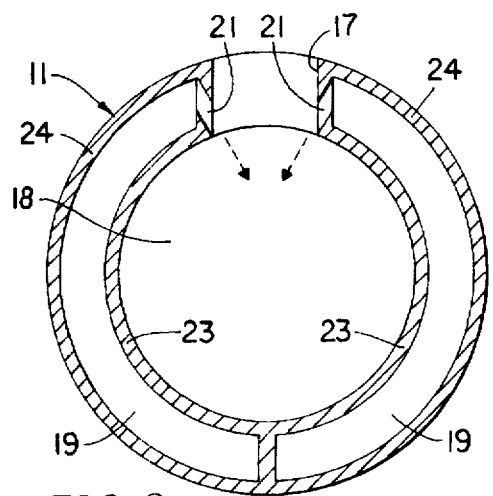
FIG. 9 is a cross-sectional view of another alternate embodiment of the apparatus showing a slit angle of approximately 60 degrees.
Figure 10:
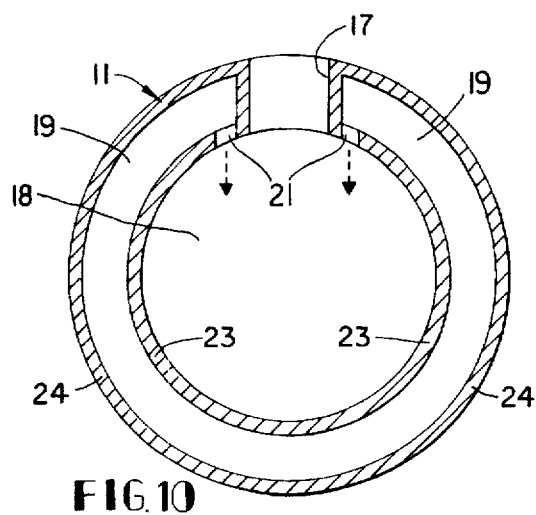
FIG. 10 is a cross-sectional view of another alternate embodiment of the apparatus showing a slit angle of approximately 90 degrees.
Figure 11:
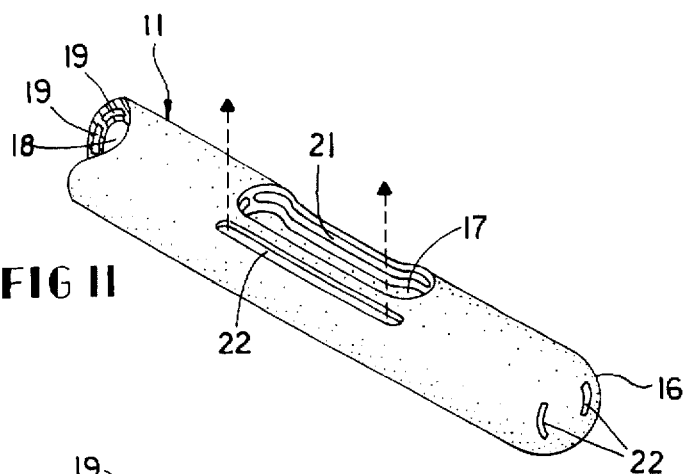
FIG. 11 is a perspective view of an alternate embodiment of the apparatus.
Figure 12:
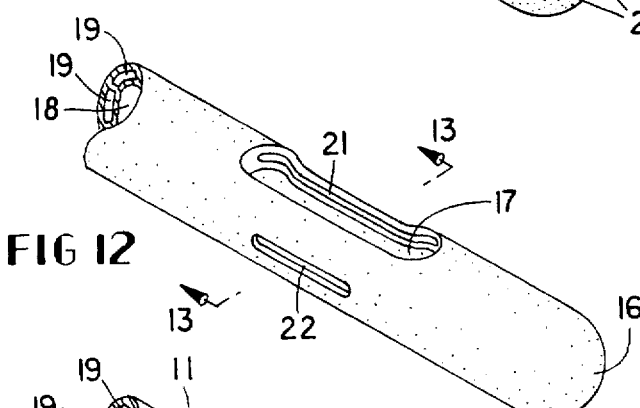
FIG. 12 is a perspective view of another alternate embodiment of the apparatus.

In alternate embodiments shown in FIGS. 8–10, the slits 21 can be angled away from the plane of the ostium toward the lumen 18 at any angle between 0–90 degrees. The angle of the sprays will enable a pulling force to hold the tissue within member 11 and assist in tissue removal after excision. Slits 21 are preferably between about 0.0001–0.5 mm wide, but this can vary depending on the particular tissue for which the present invention is utilized and the size of the member. Slit-type openings of the present invention have superior tissue cutting qualities compared to the nozzle-type openings of prior art devices. This results from the elongated cutting surface of the spray which acts to slice the tissue across substantially its full width within the ostium rather than to poke holes to break the tissue apart as seen in prior art devices.

In another embodiment, member 11 can have optional apertures 22 which open through outer wall 24 of the member to allow pressurized fluid from channels 19 to pass directly into the tissues, which aids in breaking apart the tissue prior to pulling it within the ostium. Apertures 22 can be have any desired shape and can be located along the length of member 11, some examples of which are illustrated in FIGS. 11–15, and/or at the distal end, as illustrated in FIGS. 11, 16, and 20–22. Additionally, any number of apertures 22 can be included. The present invention can also have more than two channels 19, best illustrated in FIGS. 6, 13, and 15. In the embodiment utilizing one source of pressurized fluid 14, multiple channels 19 and apertures 22 are optional. However, where at least two sources of pressurized fluid are used, multiple channels are desirable to take advantage of certain unique features of the present invention, discussed below.

In operation, pressurized fluid is forced through channels 19, out slits 21 and across ostium 17 such that the fluid flow across the ostium from the slits is almost 360 degrees along the circumference of the ostium. The opposing fluid flows are applied simultaneously across the ostium which act to prevent the tissue from being pushed away by either flow as it is cut, and in conjunction with a suction force act to hold the tissue within the ostium. The excised tissue is then sucked down the lumen for removal. In an embodiment using angled slits, the fluid forces act as a washing mechanism to "clean" suctioned tissues and limit residual free fats to reduce scarring by preventing tissue from escaping back into the body of the patient.

The present invention can utilize a continuous stream from both slits, synchronized pulsations from both slits, alternating pulsations, or any combination thereof. If pulses are used, the pulse frequency is widely variable and can range from 1 pulse per second to 10,000 pulses per second. The fluid pressure can range from 2 to 10,000 psi. The frequency and intensity of the sprays can be varied, and can be greater from one slit than the other, i.e., one stream stays on longer than other stream. The present invention can have a variable alternating frequency of pulsations between 1 per second to 100,000 per second. The present invention can also utilize alternating sprays to simply vibrate the tissue with a fluid motion, which breaks apart the tissue while minimizing damage to nearby tissues. Additionally, in an embodiment having apertures 22, the same parameters described above would also apply.

The present invention can be used to remove tumors, arterial blockages, fat, as well as many other undesirable tissues. The desired parameters discussed above can be tailored for the particular procedure performed. For example, alternating fluid pulsations at or near the natural frequency of the tissue to be removed can be selected to allow specific tissue removal without damaging surrounding tissues having different natural frequencies. In some tissues many different frequencies and forces may be necessary, thus the device will be able to continually change each variable to enhance removal. This can be done by varying the intensity, frequency and pattern of flow in a programmed pattern, such as a sine wave, with all variables fluctuating independently to meet all the natural frequencies of a given tissue to optimize tissue removal.

In an embodiment utilizing multiple sources of pressurized fluid, multiple channels 19 allow a variety of uses. For example, if a higher pressure is desired through the slits than through the apertures, one source of pressurized fluid could send the fluid into the upper channels 19 of FIG. 13 or 15 and lower pressurized fluid through lower channels 19. Additionally, this allows for fluids having different properties to be used. Alternating means (not shown) can be included in the embodiment for sending alternating pulses of pressurized fluid through complementary channels 19, however, separate pressurized sources allow for a greater variety of uses.

It is to be understood that the form of the invention shown is a preferred embodiment thereof and that various changes and modifications may be made therein without departing from the spirit of the invention or scope as defined in the following claims.

Having set forth the nature of the invention, what is claimed is:

1. Apparatus for removing body tissues, comprising in combination:
   a) an elongated housing;
   b) a central lumen extending within said housing along the length thereof said lumen being adapted for connection to a remote suction source;
   c) at least one channel between said housing and said lumen wherein said channel is defined by a partition extending within said housing along the length thereof, said channel being adapted for connection to a remote source of pressurized fluid;
   d) at least one ostium in said housing defined by a wall extending between said housing and said partition, wherein said lumen is in communication with the exterior of said housing through said ostium; and
   e) a plurality of slits formed in said ostial wall wherein said channel is in communication with said ostium through said slits.

2. An apparatus as defined in claim 1 wherein said ostium is located along the length of said housing.

3. An apparatus as defined in claim 1 wherein said ostium is located at a distal end of said housing.

4. An apparatus as defined in claim 1 wherein said apparatus has at least two opposing slits formed in said wall.

5. An apparatus as defined in claim 4 wherein said slits are formed along almost the full perimeter of said wall.

6. An apparatus as defined in claim 1 wherein said apparatus has at least two non-opposing slits formed in said wall, said slits angled toward said lumen.

7. An apparatus as defined in claim 6 wherein said slits are angled between 0 and 90 degrees from a plane substantially parallel to said housing.

8. An apparatus as defined in claim 1 further comprising at least one aperture formed in said housing and providing communication between said channel and the exterior of said house.

9. An apparatus as defined in claim 8 wherein said aperture is located along the length of said housing.

10. An apparatus as defined in claim 8 where in said aperture is located at a distal end of said housing.

11. An apparatus as defined in claim 1 wherein said slits are formed substantially parallel to said housing and collectively extend almost the full perimeter of said wall.

12. An apparatus as defined in claim 1 wherein said ostium is elliptical in shape.

13. An apparatus as defined in claim 1 wherein said ostium is circular in shape.

14. An apparatus as defined in claim 1 wherein said apparatus has a plurality of dividing walls extending within said housing along the length thereof, said dividing walls extending between said housing and said partition to form a plurality of longitudinal channels between said housing and said lumen adapted for connection to at least one remote source of pressurized fluid.

15. An apparatus as defined in claim 1 wherein said housing is rigid.

16. An apparatus as defined in claim 1 wherein said housing is flexible.

17. An apparatus as defined in claim 1 wherein said slits are between about 0.0001 to 0.5 mm wide.

18. Apparatus for removing body tissues, comprising in combination:
   a) an elongated housing;
   b) a lumen extending within said housing along the length thereof, said lumen being adapted for connection to a remote suction source;
   c) at least one opening in said housing wherein said lumen is in communication with the exterior of said housing through said opening; and
   d) means for cutting tissue as the tissue enters into said housing through said opening, said cutting means comprising opposing sprays of pressurized fluid.

19. Apparatus as defined in claim 18 wherein said opposing sprays impact tissue within said opening from substantially 360 degrees.

20. Apparatus for removing body tissues, comprising in combination:
   a) an elongated housing;
   b) a lumen extending within said housing along the length thereof, said lumen being adapted for connection to a remote suction source;
   c) at least one channel extending within said housing along the length thereof between said housing and said lumen, said channel being adapted for connection to a remote source of pressurized fluid;
   d) at least one opening in said housing defined by a wall extending from said housing toward said lumen wherein said lumen is in communication with the exterior of said housing through said opening; and
   e) at least two opposing apertures formed in said wall wherein said channel is in communication with said opening through said apertures.

21. An apparatus as defined in claim 20 wherein said apertures are formed along almost a full perimeter of said wall.

22. An apparatus as defined in claim 20 wherein said apertures are angled between 0 and 90 degrees from a plane substantially parallel to said housing toward said lumen.

23. An apparatus as defined in claim 20 wherein said apparatus has a plurality of dividing walls extending within said housing along the length thereof, said dividing walls forming a plurality of longitudinal channels between said housing and said lumen adapted for connection to at least one remote source of pressurized fluid.

* * * * *